United States Patent [19]
Allen et al.

[11] Patent Number: 5,015,845
[45] Date of Patent: May 14, 1991

[54] ELECTROSPRAY METHOD FOR MASS SPECTROMETRY

[75] Inventors: Mark Allen, Sugarland; Marvin L. Vestal, Houston, both of Tex.

[73] Assignee: Vestec Corporation, Houston, Tex.

[21] Appl. No.: 531,872

[22] Filed: Jun. 1, 1990

[51] Int. Cl.$^5$ .............................................. H01J 49/26
[52] U.S. Cl. ................................... 250/288; 250/282; 250/281
[58] Field of Search ................... 250/288, 288 A, 282, 250/281

[56] References Cited

U.S. PATENT DOCUMENTS

| | | |
|---|---|---|
| 4,023,398 | 5/1977 | French et al. ........................ 250/281 |
| 4,160,161 | 7/1979 | Horton ................................. 250/288 |
| 4,209,696 | 6/1980 | Fite ..................................... 250/288 |
| 4,531,056 | 7/1985 | Labowsky et al. ................. 250/282 |
| 4,542,293 | 9/1985 | Fenn et al. .......................... 250/288 |
| 4,842,701 | 6/1989 | Smith et al. ......................... 250/288 |
| 4,885,076 | 12/1989 | Smith et al. ........................ 250/288 |

OTHER PUBLICATIONS

Article—"New Developments in Biochemical Mass Spectrometry: Electrospray Ionization", Smith et al., American Chem. Society, 1990.

*Primary Examiner*—Bruce C. Anderson

[57] ABSTRACT

Improved techniques are provided for forming ionized molecules from electrosprayed droplets for analysis by a mass spectrometer. A high voltage is applied to a capillary tube for spraying droplets at substantially atmospheric pressure or above, and the electrosprayed droplets contain sample solute of interest and solvent. The electrosprayed droplets are passed into an ion generating chamber which is maintained at a pressure in the range of from 0.1 Torr to 10 Torr. The walls of the ion generating chamber are controllably heated to a temperature which will desolvate the droplets and produce ionized molecules of interest for analysis by the mass spectrometer. The electrospray technique does not rely upon a countercurrent heated gas flow, and provides a particularly simple and inexpensive means to couple electrospray ionization to either quadrupole or magnetic mass analyzers.

20 Claims, 2 Drawing Sheets

ELECTROSPRAY METHOD FOR MASS SPECTROMETRY

BACKGROUND OF THE INVENTION

1. Field of the Invention

The present invention relates to techniques for producing ions for the determination of molecular weights of chemical compounds by mass spectrometry. More particularly, the invention relates to improved electrospray ionization techniques for producing molecular ions at atmospheric pressure, and for efficiently transmitting such ions into the vacuum of a mass spectrometer without introducing uncontrolled changes in mass due to fragmentation or clustering with solvent or other neutral molecules.

2. Description of the Background

Mass spectrometry is a well known technique for obtaining a molecular weight and structural information on chemical compounds. According to mass spectrometry, molecules may be "weighed" by ionizing the molecules and measuring the response of their trajectories in a vacuum to electric and magnetic fields. With traditional ionization techniques such as electron ionization, photo-ionization, and chemical ionization, the applications of mass spectrometry were limited to relatively low molecular weight, thermally stable neutral molecules.

Improved "soft" ionization techniques, such as field desorption, thermospray, and electrospray, have recently been developed which produce intact molecular ions from high molecular weight, ionic and thermally labile molecules. As a result, applications of mass spectrometry have become increasingly important in many areas, such as biological research, where detection and characterization of such materials is often required. While each of these soft ionization techniques may be preferred for certain applications, electrospray is one of the most promising techniques for producing molecular weight information on large biopolymers, such as proteins.

Electrospray ionization techniques were first proposed in the late 1960's. A sample solution containing molecules of interest and a solvent is pumped through a hypodermic needle and into an electrospray chamber. An electrical potential of several kilovolts may be applied to the needle for generating a fine spray of charged droplets. According to UK patent specification 1,246,709, the droplets may be sprayed at atmospheric pressure into a chamber containing a heated gas to vaporize the solvent. Alternatively, the needle may extend into an evacuated chamber, and the sprayed droplets then heated in the evacuated chamber by an infared filament. In either case, ions are focused into a beam, which is accelerated by an electric field gradient, and the ions then analyzed in a mass spectrometer.

Significant disadvantages are encountered if an electrospray is discharged into an evacuated chamber. The charged droplets are not retarded from migrating toward the chamber walls, thereby increasing the possibility of discharge and disruptions to the spray. U.S. Pat. No. 4,209,696 teaches an electrospray technique which occurs at atmospheric pressure or above, and the produced ions are input to a mass analyzer.

Although the electrospray is preferably formed at atmospheric pressure, mass spectrometers operate within a vacuum chamber. A vacuum housing for a mass spectrometer typically includes a plurality of lenses in a vacuum chamber, which is maintained at a sufficiently low pressure that collisions of the ions with neutral molecules is unlikely. The chamber is typically heated to about 100° C. to prevent condensation on the lenses and to keep them clean. When a gas at atmospheric pressure passes through a small orifice into an evacuated chamber, it expands rapidly in all directions and the pressure in the expanding gas decreases in proportion to the square of the distance from the orifice inside the vacuum chamber. The role of the lenses is to focus the ions into a beam for analysis by the mass analyzer, but the lenses are relatively ineffective at influencing the trajectory of the ions until the pressure in the expanding gas is sufficiently low that the mean free path for collisions of ions with neutral molecules is larger than the critical dimensions of the lenses. As a result, a large fraction of the ions produced in the electrospray chamber may be swept away by the expanding gas and removed by the vacuum pumps. Only a small fraction of the produced ions are focused by the lenses and transmitted to the mass analyzer for detection. Accordingly, this low transfer of ions to the mass analyzer produced by electrospray substantially limits the sensitivity of the electrospray/mass spectrometer technique.

Another significant problem with electrospray concerns the condensation of the expanding jet and clustering of the ions. To reduce this problem, heated counterflow gases are commonly employed to vaporize sprayed droplets and desolvate ions at atmospheric pressure. Since the heated counterflow gases remove much of the solvent vapor from the stream of gas before being drawn into the vacuum chamber, this technique increases the concentration of ions of interest in the vacuum chamber. U.S. Pat. No. 4,023,398 teaches a technique whereby ions pass through an orifice into a vacuum chamber, while a gas curtain upstream from the orifice reduces transmission of solvent vapor into the vacuum chamber. The gas is heated to hasten evaporation of the solvent from the droplets, thereby producing desolvated ions at substantially atmospheric pressure U.S. Pat. No. 4,531,056 teaches a similar technique, whereby an inert gas is introduced into the electrospray chamber in a direction opposite to a flow from the capillary. The electrospray chamber remains at or slightly greater than atmospheric pressure. Ions of interest are produced within the electrospray chamber, and the inert gas flow substantially reduces the concentration of solvent vapor which enters the analyzer. U.S. Pat. Nos. 4,842,701 and 4,885,076 disclose a system which combines capillary zone electrophoresis with electrospray for gas analysis of an analyte mixture. Again, the electrospray occurs at atmospheric pressure, and a heated countercurrent gas flow technique is used to desolvate the spray droplets.

While the counterflowing gas concept described above results in reasonable sensitivity, it substantially increases the complexity of the interface between the electrospray and the mass spectrometer. In order that the solvent vapor from the evaporating droplets be efficiently removed by the counterflowing gas, both the temperature and the flow rate of the gas must be carefully controlled. High gas flow rates may prevent some ions with low mobility from entering the analyzer, while low gas flow rates or reduced gas temperature may not sufficiently desolvate the ions. The counterflowing gas flow rate and temperature are typically optimized for each analyte and solvent. Accordingly, much trial and error time is necessary to determine the optimum gas flow rate and temperature for each particular analyte utilizing a particular electrospray device and a particular mass spectrometer.

A major limitation of these prior art electrospray devices is that, for a given set of operating conditions, a stable electrospray can only be achieved within a rather narrow range of liquid input flow rates and liquid compositions. In particular, these prior art techniques are not practical for electrospraying pure water, or water containing modest amounts of ionic buffers. As a result, these systems cannot be used effectively with standard liquid chromatography procedures commonly used in gradient elution from reversed phase, which require continuous modification of the mobile phase composition from 100% water to either 100% methanol or acetonitrile.

The disadvantages of the prior art are overcome by the present invention, and improved techniques are hereinafter disclosed for improving the stability, reliability, and sensitivity of electrospray mass spectrometry so that it can be readily coupled to standard micro-bore HPLC techniques for the analysis of a wide variety of biological and other materials.

SUMMARY OF THE INVENTION

Improved methods and apparatus are provided for analyzing liquid effluent which includes a sample solute of interest and a solvent (or mixture of solvents). The solute may consist of high molecular weight organic molecules, which are input from a liquid chromatograph with either a more volatile organic solvent, such as methanol, or a less volatile, more polar solvent, such as water. The solution may also contain significant concentrations of acids or other ionic compounds chosen either to improve the separation of compounds by the liquid chromatograph or to enhance the ionization of the solutes of interest.

According to the present invention, the solution is discharged from a small needle tube into an electrospray chamber maintained at approximately atmospheric pressure. A high electrical potential is applied to the needle with respect to the housing walls to produce a spray containing highly charged droplets. The electrospray chamber may be in direct communication with ambient air, or a gas may be added to the electrospray chamber to maintain the desired atmospheric pressure within the electrospray chamber and prevent corona discharges from occurring within the electrospray chamber. All of the fluid entering the chamber (which includes the liquid and its vapor, the added gas, and residual droplets, particles, and ions) exit from the electrospray chamber through a convergent nozzle in the form of a supersonic jet. The core of this jet is aligned with a skimmer which controls fluid flow to a heated desolvation chamber, and the excess gas and vapor is pumped away by a vacuum pump connected to the housing enclosing the desolvation chamber. The electrospray housing, as well as the nozzle from the electrospray chamber, is electrically isolated from the adjacent housings so that the spray current may be conveniently monitored by measuring the current to the electrospray housing when the electrospray is operating. The electrically isolated housing also allows the nozzle to be biased at an appropriate potential relative to the skimmer and thereby assist in the transmission of ions through the nozzle-skimmer region.

Adiabatic expansion of the gas and vapor through the nozzle causes severe cooling, and as a result neutral vapor molecules condense on ions or small particles in the jet to form large cluster ions and frozen particles of solvent. Controlled heating of the desolvation chamber revaporizes these clusters and particles to produce desolvated molecular ions without introducing thermal degradation or fragmentation. Desolvated molecular ions exit from the desolvation chamber through a small aperture in a sampling cone which is affixed to but electrically isolated from the desolvation chamber. A potential applied to the desolvation housing relative to the sampling cone causes ions to drift toward the sampling orifice, thus enhancing the efficiency with which ions are withdrawn through the aperture. A vacuum pump is connected to the desolvation chamber to pump away a sufficient quantity of the input gas and vapor to maintain the chamber at a low enough pressure that significant adiabatic cooling and ion clustering does not occur at the exit from this chamber, while also maintaining a sufficently high pressure so that efficient heat transfer to the input ion clusters and neutral particles can occur. A typical operating pressure for the desolvation chamber is about 0.5 torr, and depending on the orifice size, this chamber may typically be maintained in the range from 0.1 to 1.0 torr. The temperature of this chamber usually should be maintained at least 120° C., and preferably between 150° C. and 250° C.

It is also desirable to control the temperature of the electrospray chamber to maintain a stable spray over a wide range of liquid flows and compositions. The optimum temperature varies to some extent with conditions, but is typically about 50° C. Heat may be coupled by thermal conduction from the desolvation chamber to the electrospray chamber, and temperature control means are provided for either heating or cooling the electrospray chamber to maintain the desired operating temperature.

It is an object of the present invention to provide a highly efficient electrospray ionization interface for mass spectrometry which is at the same time simple, inexpensive, and reliable.

Another object of the invention is to provide a practical interface suitable for use between micro-bore HPLC and electrospray ionization mass spectrometry for conducting reversed phase separations of biological samples.

It is a further object of the invention to provide a highly sensitive system suitable for producing and detecting multiply charged molecular ions from proteins and other biopolymers, and thus accurately determining their molecular weights.

It is feature of this invention to provide stable molecular ion currents from samples input as solutes in liquid solution over a wide range of liquid flow rates and compositions typically ranging from 0.5 to 200 microliters/min and from 100% water to 100% organic.

It is another feature of the invention that all of the material input to the electrospray chamber exits through a converging nozzle to produce a supersonic jet.

It is a further feature of the present invention that the position of the electrospray needle can be adjusted relative to the entrance of the converging nozzle to maximize the ion extraction efficiency.

It is also a feature of the invention that the temperature of the electrospray housing and the input gas flow rate can be controlled to stabilize the electrospray current for a wide range of liquid flow rates and compositions.

Still another feature of the present invention is that the distance between the nozzle and skimmer can be adjusted to maximize the ion transmission efficiency.

It is a further feature of this invention that an electrical potential difference can be applied between the nozzle and skimmer to maximize ion transmission efficiency.

Yet another feature of the present invention is that the temperature and pressure of the desolvation chamber may be controlled to desolvate ion clusters produced in the supersonic jet expansion and efficiently transport desolvated ions to the mass spectrometer for analysis.

An additional feature of this invention is that the ion extraction or sampling cone is electrically isolated from the desolvation chamber, so that an electrical potential difference can be applied to maximize ion extraction.

It is an advantage of the present invention that the sensitivity for detecting multiply charged molecular ions is significantly improved.

It is another advantage of this invention that it employs relatively small, inexpensive vacuum pumps to remove the excess gas and solvent vapor and to produce the vacuum needed for operation of the mass spectrometer.

Yet a further advantage of this invention is that the overall ionization and detection efficiency increases with the mass of the sample molecule.

These and further objects, features, and advantages of the present invention will become apparent from the following detailed description, wherein reference is made to the figures in the accompanying drawings.

BRIEF DESCRIPTIONS OF THE DRAWINGS

DETAILED DESCRIPTION OF PREFERRED EMBODIMENTS

Figure 1:
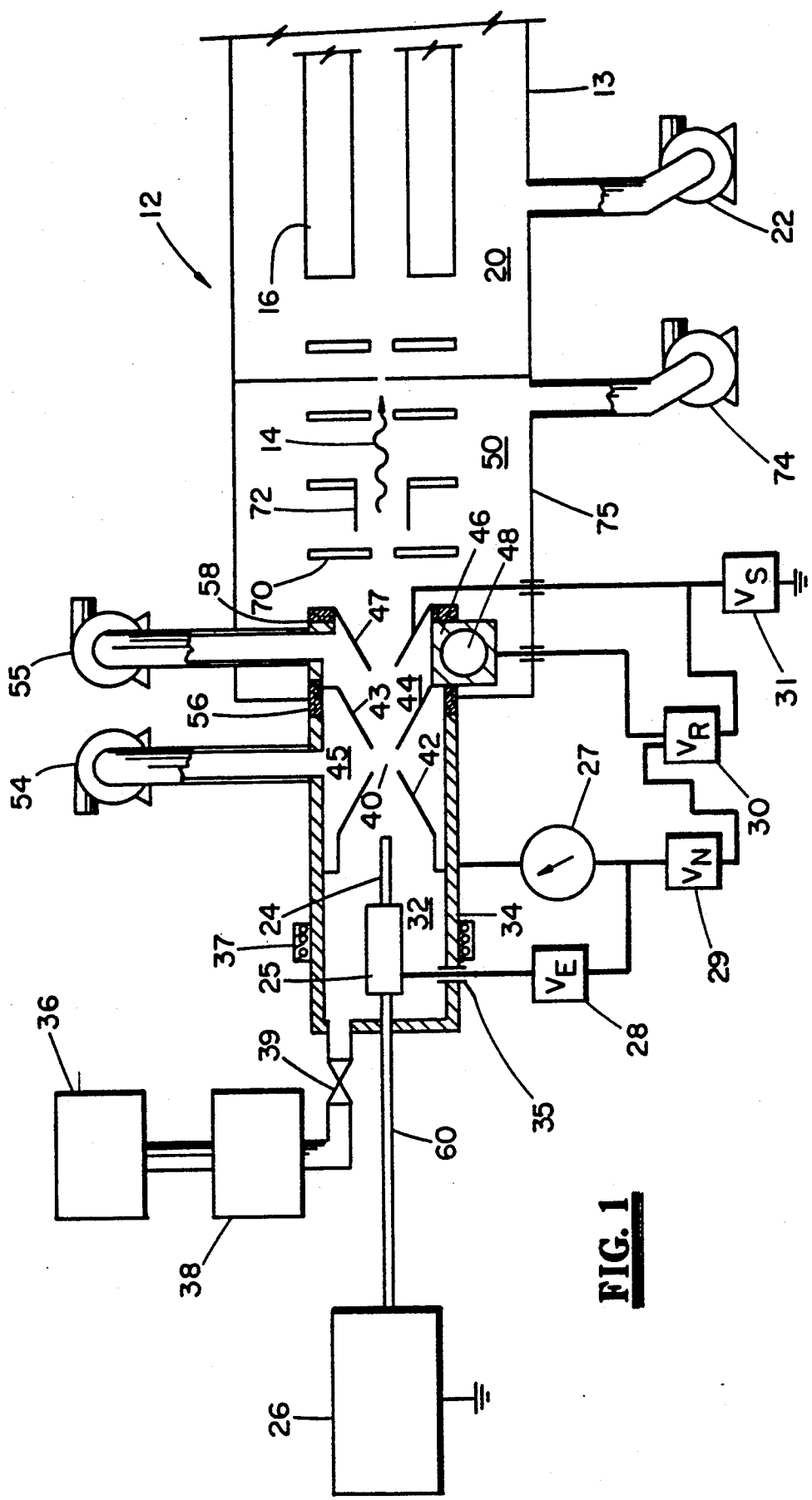
FIG. 1 is a simplified pictorial view and block diagram of a preferred embodiment of a combined micro-HPLC/electrospray ionization interface for mass spectrometry.

FIG. 1 depicts a preferred embodiment of the present invention suitable for interfacing between a micro-bore HPLC unit 26 and a quadrupole mass spectrometer 12. Samples injected into the HPLC are separated on a column, and elute sequentially in a flow of liquid which typically may be in the range of from 0.5 to 200 microliters per minute. The liquid composition may vary from essentially pure water to essentially pure organic solvent, such as methanol, and both solvent components may contain additives such as organic acids or inorganic buffers.

The present invention is thus used to detect and determine the molecular weights of samples present in this liquid flow, even though the sample material may be present in very minute amounts. The mass spectrometer or analyzer 12 may be of various types, although a quadruple mass analyzer suitable for analysis of liquid chromatograph is preferred. Accordingly, the analyzer 12 may receive a beam 14 of ions centrally passing between four charged rods 16 which create an electrical field within the analyzer. According to their mass-to-charge ratio, the ions are either deflected or transmitted by the electrical field, and the transmitted ions may be detected by a standard electron multiplier detector (not shown). For the analyzer to properly operate, the electric or magnetic field which deflects the ions is housed within a chamber 20 which is maintained at a vacuum of less than about $10^{-5}$ Torr by vacuum pump 22 capable of displacing approximately 150 liters per second at atmospheric pressure.

The liquid effluent from the micro-HPLC unit 26 is transferred to an electrospray needle 24 through a length of fused silica tubing 60, which may be on the order of 25 to 150 microns in internal diameter and from 0.3 to 3 meters in length. A voltage typically in the range of from 1.5 to 5 KV is applied to the electrospray needle 24 by a high voltage supply, which may be connected to the electrically conductive fitting 25 joining the fused silica tubing 60 to the electrospray needle 24. The dimensions of the fused silica tube are choosen to provide a sufficient electrical resistance between the needle and the HPLC unit 26, which is grounded. While liquid is supplied to the electrospray needle, the voltage $V_E$ relative to the electrospray housing 34 is adjusted until a stable electrospray is produced as indicated by the meter 27 which measures the electrical current collected on the electrospray housing 34. A gas, which may be ambient air or nitrogen, is added to the electrospray chamber 32 in sufficient quantity to maintain the chamber at approximately atmospheric pressure. The gas may be provided from pressurized supply 36, and may be either heated or cooled by temperature control unit 38. The flow rate of gas to the electrospray chamber 32 is controlled by valve 39.

All fluids entering the chamber 32 escape through the discharge port 40 in the nozzle 42, which is aligned with the axis of the electrospray needle 24 within the chamber 32. The size of the aperture 40 is controlled to maintain substantially atmospheric pressure within the chamber 32, since a reduction in pressure, e.g., to less than 100 Torr, would enhance discharge of the sprayed droplets into the walls of the housing 34. The temperature of the electrospray chamber 32 may be maintained at a desired value by means of a heat exchanger jacket 37 surrounding the chamber and/or by passing the added gas through a heat exchanger 38 where the necessary heat is supplied or removed. The optimum temperature of the chamber 32 depends to some extent on the composition and flow rate of the liquid, as well as on the internal diameter of the electrospray needle, but appropriate temperatures are typically in the range of from 40° to 60° C. While the electrospray chamber 32 may be maintained at room temperature to achieve a uniform electrospray when the solvent is volatile, the chamber 32 preferrably is heated to about 50° C. if water is used as the solvent. This warming of the electrospray solution reduces the surface tension for the sprayed droplets, so that a uniform spray may be obtained with nominal heating of the water.

Electrospray produces a fine spray of highly charged droplets. As these droplets vaporize at atmospheric pressure, molecular ions are released from the droplets into the gas phase. A portion of these ions and charged droplets impinge on the housing 34 to produce the current measured by the meter 27. The remainder of the ions, any residual charged droplets or particles, and the added gas exit the electrospray chamber through a converging nozzle 42 into an evacuated chamber 45.

The minimum diameter of the nozzle is typically in the range of from 0.3 to 0.5 mm, and the total gas flow through the nozzle 42 is typically from 1 to 2 L/min. Under these conditions, essentially all of the liquid droplets are vaporized before they reach the nozzle exit.

A supersonic jet is formed as the result of expansion through the nozzle 42, and the core of this jet is sampled by a skimmer 43 placed in line with the axis of the jet. The chamber between the nozzle and skimmer is evacuated by a mechanical vacuum pump 54 of modest capacity, e.g., a pump with a capacity of 12 cubic meters/hour is satisifactory with a 0.4 mm nozzle. The fraction of the supersonic jet which is sampled by the skimmer 43 depends on the skimmer aperture diameter and distance downstream. Skimmer aperture diameters in the range of 0.6 to 1.0 mm are generally satisfactory, and the distance between nozzle and skimmer is adjustable, as explained subsequently.

The fluid in the supersonic free jet expansion is adiabatically cooled to a low temperature in the course of the expansion. As a result, solvent vapor molecules condense on the ions or other condensation nuclei present in the jet to form charged and neutral clusters which are very much larger in mass-to-charge ratio than can be analyzed by conventional mass spectrometers. Thus, if such a free jet expansion is coupled directly to the vacuum of a mass spectrometer, such as was done in the early work of Dole and coworkers, essentially no molecular ions within the mass range of the mass spectrometer are observed. In the present invention, this problem is overcome by placing a desolvation chamber 44 between the free jet expansion and the mass spectrometer. This desolvation chamber is maintained at a sufficiently high pressure and temperature that enough heat is transferred to the clusters and particles so that they approach thermal equilibrium with the gas in the desolvation chamber.

The desolvation chamber 44 is preferrably maintained at a pressure between 0.1 and 1.0 Torr, and at a temperature of from 150° and 250° C. A satisfactory operating pressure is maintained by coupling this chamber to a mechanical vacuum pump 55 with a nominal capacity of 12 cubic meters per hour through a pumping tube having approximately a 1 cm inside diameter. The chamber 44 is heated by a heater cartridge 48 imbedded in the chamber wall 46, and a thermocouple (not shown) attached to the chamber indicates the temperature and couples to a temperature controller to adjust the heater power to maintain the desired temperature. An electrical power supply to the heating elements 48 is regulated by a controller, which is responsive to the temperature sensors. The temperature of the desolvation chamber 44 is thus closely controlled in a manner as disclosed in U.S. Pat. No. 4,814,612. The reliable control of the ionization process is provided in a manner which is not significantly dependant on the composition or flow rate of the sprayed effluent. Accordingly, little if any equipment modification and trial and error refinements to the controls are required to achieve high detector sensitivity for various compositions and flow rates.

Ions exit from the desolvation chamber 44 through a sampling cone 47 located on axis with the skimmer 43. This ion exit or sampling cone is electrically isolated from the housing 46 so that a potential difference can be applied to cause ions to drift toward the sampling aperture and thus increase the fraction of ions that exit through the aperture to the mass analyzer. The ions exit from the desolvation chamber 44 into a standard lens system 72 used for focusing ions into the mass analyzer 12. The potential on the ion exit cone 47 relative to the mass analyzer 12 affects the energy of the ions which are subsequently analyzed by the spectrometer 12. The lens chamber 50 is evacuated by a diffusion pump 74 with a nominal capacity of 300 liter/sec, and with an ion exit aperture of 1 mm diameter. This pump sufficient to maintain a pressure of less than $1 \times 10^{-4}$ Torr within the lens housing 75. The ion beam 14 then passes through an aperture into the mass analyzer housing 13. This housing is evacuated by a 150 L/sec pump 22 which maintains the pressure below $10^{-5}$ Torr.

The voltage controller 28 depicted in FIG. 1 thus is regulated to maintain a high voltage potential $V_E$ between the electrospray needle 24 and the electrospray housing. The current flowing to the housing 34 is monitored by sensor 27. Voltage regulator 29 maintains a voltage potential $V_N$ between the electrospray housing 34 (and thus also nozzle 42) and the housing 46 which defines the desolvation chamber 44. Insulator 56 thus provides electrical isolation between housing 34 and housing 46. Regulator 30 maintains another electrical potential $V_R$ between the housing 46 and the sampling cone 47, which is isolated from housing 46 by insulator 58. Finally, regulator 31 maintains a potential $V_S$ on the sampling cone 47 relative to ground. Electrical insulators 35 are generally depicted for isolating the electrical lines when passing through housing walls.

Figure 2:
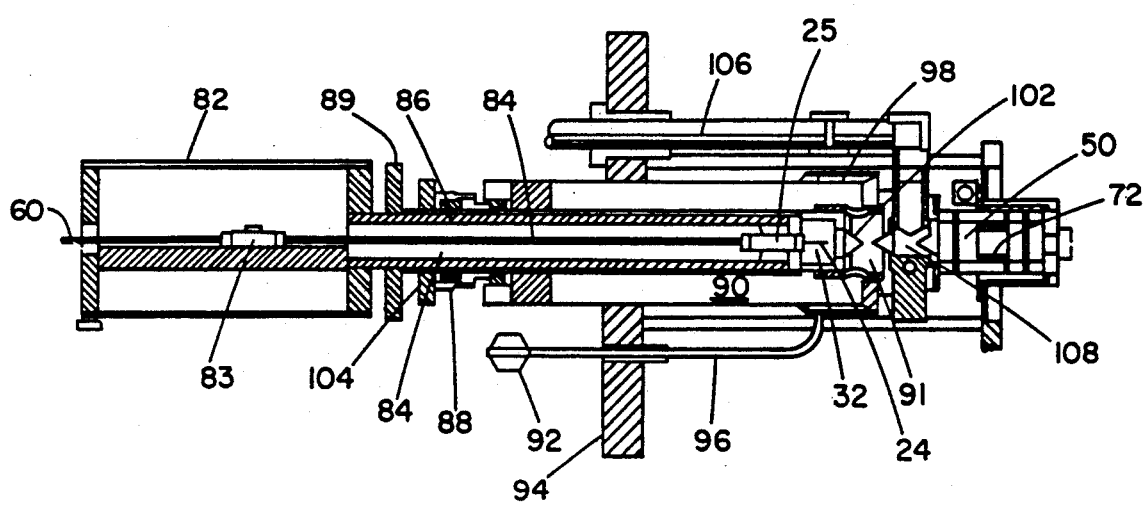
FIG. 2 is a cross-sectional view of one embodiment of an electrospray ionization interface according to the present invention.

FIG. 2 illustrates another embodiment of the electrospray and ionization interface suitable for use between a liquid chromatograph and a mass analyzer. The effluent sample flows through fused silica line 60 into probe 82, and the effluent is charged by a high voltage supply 28 connected to tube coupling 83 which joins the fused silica line 60 to a length of stainless steel (or other conductive metal) capillary 84 connected to the coupling 25, which is joined to the electrospray needle 24. Gas may be passed through the annulus 84 formed between the housing 86 and the electrospray needle 24. The coupling 25 is provided for mounting the tip of the electrospray needle. The electrospray chamber 32 is maintained at substantially atmospheric pressure, and the position of the needle discharge tip relative to the chamber 32 is selectively controlled by nut 89.

The vacuum seal assembly 88 and a vacuum pump (not shown in FIG. 2) maintain the primary pump out cavity 90 and thus the first chamber 91 of the two stage vacuum system at the desired pressure. The temperature control unit 92 is provided outside the vacuum flange 94, and coolant line 96 is provided for heating or cooling the annular jacket 98 to a desired low temperature. The position of the discharge nozzle 102 relative to the chamber 91 may be controlled by adjustable nut 104. The secondary pumpout line 106 is connected to another vacuum pump (not shown) to maintain the second chamber 108 at the desired pressure to desolvate the sprayed droplets. The ions source chamber 50 includes a stack of ion lenses 72, as previously discussed.

Figure 3:
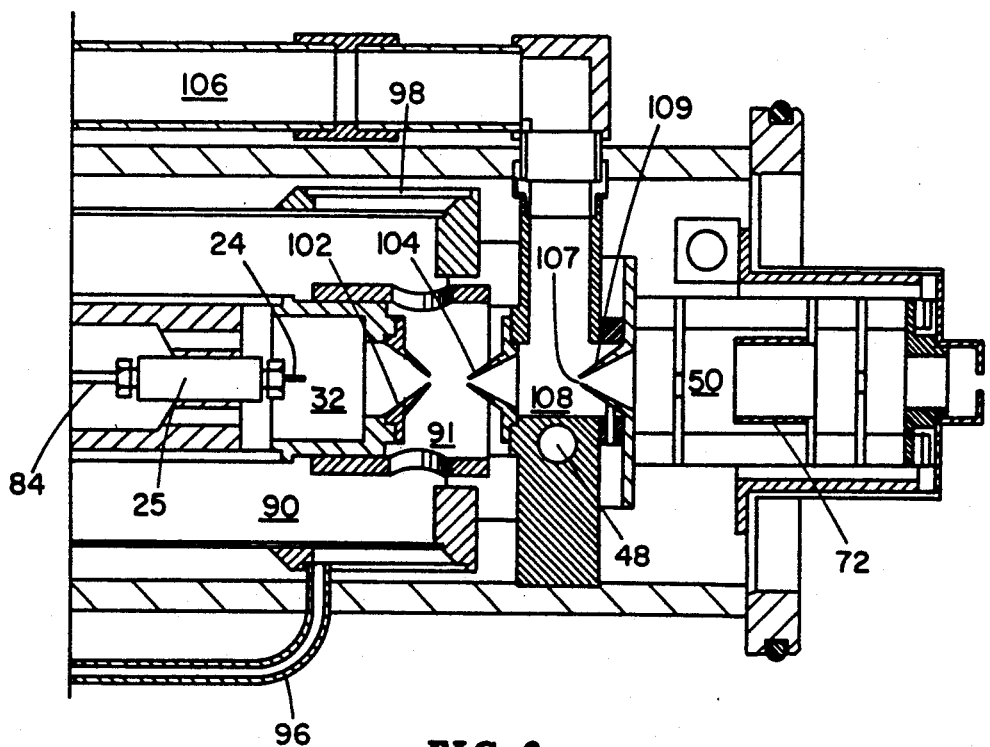
FIG. 3 is a detailed cross-sectional view of a portion of the interface shown in FIG. 2.

FIG. 3 depicts in greater detail the needle discharge tip 24 in the electrospray chamber 32. Nozzle 102 which defines the discharge port from the electrospray chamber 32 may be maintained at from +200 to +500 volts, while the skimmer 104 from the chamber 91 may be maintained at from +20 to +60 volts. The vacuum pump maintains a pressure of about 5 Torr in the chamber 91, while another vacuum pump maintains a pressure of about 0.5 Torr in the chamber 108. The chamber 108 is heated by a plurality of heating elements 48, and temperature sensors are provided to control the heating of the chamber 108, as previously discussed. The sampling cone 109 having an aperture 107 may be maintained at a voltage of from +5 volts to +20 volts, and the ion source chamber 50 may be maintained at a pressure of about $10^{-4}$ Torr by a vacuum pump having a capacity of about 400 liters per second. All of the voltages indicated above are those used for producing positive ions. The apparatus also may be used for producing negative ions, and all that is required is to invert the polarity of all of the power supplies.

According to the method of the present invention, various solvents including water may be passed through the liquid chromatograph to extract the solvent of interest from the LC columns. The interface as disclosed herein may be used to electrospray this effluent at substantially atmospheric pressure or above by applying the high voltage to the capillary tube. A gas, such as air or nitrogen, may be added to the electrospray chamber to maintain the desired pressure in the electrospray chamber, and the discharged port is sized accordingly.

According to a preferred embodiment of the invention as shown in FIGS. 2 and 3, the electrospray needle, nozzle, skimmer, sampling cone, ion lenses and analyzer are coaxially aligned to maintain high efficiency. A transverse arrangement may be used, however, as disclosed in copending U.S. Application Ser. No. 07/514,658 filed Apr. 24, 1990.

A substantial amount of effluent, e.g. 30 microliters or more, may be electrosprayed, and all this fluid may then passed directly to the desolvation chamber. Alternatively, a two staged vacuum unit may be employed, as shown in FIGS. 2 and 3, so that some solvent vapor is removed prior to the droplets entering the temperature controlled ion generating or desolvation chamber. The temperature within the desolvation chamber is closely monitored and controlled to produce desolvated ions for analysis by the analyzer 12, and this control may occur automatically with little if any regard to the composition or flow rate of the electrosprayed effluent.

The foregoing disclosure and description of the invention is illustrative and explanatory of the techniques of the present invention, and various changes in the size and shape of the interface, as well as in the details of the illustrated construction, may be made within the scope of the appended claims and without departing from the spirit of the invention.

What is claimed is:

1. Apparatus for converting a liquid effluent including sample solute of interest and solvent into ionized molecules for analysis of the sample by a mass spectrometer, the apparatus comprising:
   (a) an electrospray unit for receiving liquid effluent and for discharging charged droplets, the electrospray unit including
      (i) an electrospray housing defining an atmospheric pressure electrospray chamber therein,
      (ii) a capillary tube for passing liquid effluent therethrough, the capillary tube having an exit within the electrospray chamber for discharging sprayed droplets containing sample solute of interest and solvent,
      (iii) a high voltage source for applying a high voltage to the capillary tube to produce charged sprayed droplets containing sample solute of interest and solvent, the charged sprayed droplets vaporizing within the electrospray housing to produce ions, and
      (iv) a nozzle defining a portion of the electrospray housing and having a discharge port for outputting the ions and solvent vapor from the electrospray chamber, the discharge port being sized to maintain substantially atmospheric pressure within the electrospray chamber during spraying;
      (v) a first electrical biasing unit for applying a biasing voltage to the nozzle; and
   (b) an ion generating unit for receiving clusters of ions including condensed solvent from the electrospray unit and for discharging ionized molecules to the mass spectrometer, the ion generating unit including
      (i) an ion generating housing defining an ion generating chamber therein,
      (ii) an ion generating unit vacuum pump for maintaining pressure within the ion generating chamber in the range of from 0.1 Torr to 10 Torr,
      (iii) a temperature sensor for monitoring the temperature within the ion generating chamber,
      (iv) a heating unit responsive to the temperature sensor for heating the ion generating housing to a temperature of at least 120° C. to vaporize condensed solvent in the clusters of ions and produce desolvated ionized molecules of interest for analysis by the mass spectrometer,
      (v) a sampling cone having passage therethrough for discharging ionized molecules from the ion generating chamber, and
      (vi) a second electrical biasing unit for applying a biasing voltage to the sampling cone relative to the nozzle of the electrospray unit.

2. The apparatus as defined in claim 1, wherein:
   the ion generating housing is electrically isolated from the sampling cone; and
   a third biasing unit for applying a biasing voltage to the ion generating housing relative to the nozzle of the electrospray unit.

3. The apparatus as defined claim 1, wherein the discharge port from the nozzle is adjoining the ion generating chamber, such that substantially all materials passing through the discharge port enter the ion generating chamber 4. The apparatus as defined in claim 1, further comprising:
   gas supply means for inputting a gas into the electrospray chamber; and
   valve means for controlling the input gas to maintain substantially atmospheric pressure within the electrospray chamber.

5. The apparatus as defined in claim 1, wherein the voltage source applies a voltage of from 1 KV to 10 KV to the capillary tube with respect to the ion generating housing.

6. The apparatus as defined in claim 1, further comprising:
   adjusting means for selectively moving the capillary tube with respect to the electrospray housing.

7. The apparatus as defined in claim 1, further comprising:
   an evacuated chamber spaced between the electrospray chamber and the ion generating chamber:
   a skimmer having an exit aperture for discharging fluid from the evacuated chamber to the ion generating chamber; and a pump for maintaining pressure within the evacuated chamber within a selected range and for removing solvent vapor from the apparatus.

8. The apparatus as defined in claim 7, further comprising:
an adjustment unit for selectively adjusting the spacing between the nozzle and the skimmer.

9. The apparatus as defined in claim 1, further comprising:
a temperature control unit for regulating the temperature of the electrospray housing.

10. The apparatus as defined in claim 1, wherein the electrospray unit and ion generating unit are each axially aligned with the mass spectrometer.

11. A method of converting a liquid effluent including sample solute of interest and solvent into ionized molecules for analysis by a mass spectrometer, the method comprising:
forming an electrospray chamber having a restricted discharge port therethrough;
passing liquid effluent through a capillary tube terminating within the electrospray chamber for discharging sprayed droplets containing sample solute of interest and solvent;
applying a voltage to the capillary tube to produce charged sprayed droplets containing sample solute of interest and solvent;
maintaining the electrospray chamber at substantially atmospheric pressure or above during spraying;
applying a first biasing voltage during spraying to at least a portion of an electrospray housing which defines the restricted discharge port;
forming in an ion generating housing which defines an ion generating chamber;
passing the charged sprayed droplets into the ion generating chamber while maintaining a pressure within the ion generating chamber within the range of from 0.1 Torr to 10 Torr;
monitoring the temperature within the ion generating chamber:
heating the ion generating housing in response to the monitored temperature to vaporize solvent in clusters of ions and produce desolvated ionized molecules of interest for analysis by the mass spectrometer;
applying a second biasing voltage to a skimmer relative to the portion of the electrospray housing and
outputting the desolvated ions through the skimmer to the mass spectrometer.

12. The method as defined in claim 11, further comprising:
heating the ion generating housing to maintain a temperature within the ion generating chamber of at least 120° C.

13. The method as defined in claim 12, further comprising:
inputting a gas to the electrospray chamber: and
controlling the quantity of input gas to maintain substantially atmospheric pressure within the electrospray chamber.

14. The method as defined in claim 13, further comprising:
controlling the temperature of the gas to regulate the temperature within the electrospray chamber.

15. The method as defined in claim 12, further comprising:
applying the voltage of from 1 KV to 10 KV to the capillary tube with respect to the ion generating housing.

16. The method as defined in claim 12, further comprising:
selectively moving the terminal end of the capillary tube within the electrospray housing.

17. The method as defined in claim 11, further comprising:
forming the electrospray chamber such that the discharge port adjoins the ion generating chamber, and substantially all fluid exiting the electrospray chamber enters the ion generating chamber.

18. The method as defined in claim 11, further comprising:
providing an evacuated chamber between the electrospray chamber and the ion generating chamber;
providing a skimmer having an exit aperture for discharging fluid from the evacuated chamber to the ion generating chamber; and
pumping gas from the evacuated chamber to maintain the evacuated chamber within a selected pressure range 19. The method as defined in claim 11, further comprising:
selectively adjusting the spacing between the portion of the electrospray housing and the skimmer.

20. The method as defined in claim 11, further comprising:
regulating the temperature of the electrospray housing to maintain the temperature within the electrospray chamber within a selected range.

* * * * *

UNITED STATES PATENT AND TRADEMARK OFFICE
CERTIFICATE OF CORRECTION

PATENT NO. : 5,015,845
DATED : May 14, 1991
INVENTOR(S) : Mark Allen and Marvin L. Vestal It is certified that error appears in the above-identified patent and that said Letters Patent is hereby corrected as shown below:

In Column 10, line 26 (Claim 1, line 44), delete the "." after "C".

In Column 10, line 46 (Claim 3, line 5), insert "." after "chamber".

In Column 10, line 65 (Claim 7, line 4), change ":" to -- ; --.

In Column 11, line 41 (Claim 11, line 26), change ":" to -- ; --.

In Column 11, line 48 (Claim 11, line 33), insert "," after "housing".

In Column 12, line 8 (Claim 13, line 3), change ":" to -- ; --.

In Column 12, line 40 (Claim 18, line 10), insert "." after "range".

Signed and Sealed this

Seventeenth Day of November, 1992

*Attest:*

DOUGLAS B. COMER

*Attesting Officer*     *Acting Commissioner of Patents and Trademarks*